United States Patent [19]
Koprowski et al.

[11] Patent Number: 6,042,832
[45] Date of Patent: Mar. 28, 2000

[54] POLYPEPTIDES FUSED WITH ALFALFA MOSAIC VIRUS OR ILARVIRUS CAPSID PROTEINS

[75] Inventors: Hilary Koprowski, Wynnewood; Vidadi Yusibov, Havertown, both of Pa.; Douglas Craig Hooper, Medford, N.J.; Anna Modelska, Wynnewood, Pa.

[73] Assignee: Thomas Jefferson University, Philadelphia, Pa.

[21] Appl. No.: 08/704,856

[22] Filed: Aug. 28, 1996

[51] Int. Cl.$^7$ .............................. A01H 1/00; A61K 39/00; C07K 14/005; C12N 5/14

[52] U.S. Cl. .................................. 424/192.1; 424/196.11; 424/199.1; 424/207.1; 424/224.1; 435/414; 435/419; 800/278; 800/280; 800/288

[58] Field of Search ................................ 800/278, 280, 800/288; 424/224.1, 192.1, 207.1, 196.11, 199.1; 435/414, 419

[56] References Cited

U.S. PATENT DOCUMENTS

| | | | |
|---|---|---|---|
| 5,041,385 | 8/1991 | Kingsman et al. | 435/320.1 |
| 5,316,931 | 5/1994 | Donson et al. | 435/172.3 |
| 5,589,367 | 12/1996 | Donson et al. | 435/172.3 |
| 5,612,487 | 3/1997 | Lam et al. | 800/205 |

FOREIGN PATENT DOCUMENTS

| | | | |
|---|---|---|---|
| 0174759B1 | 4/1991 | European Pat. Off. | C07K 17/00 |
| WO 92/18618 | 10/1992 | WIPO | C12N 7/01 |

OTHER PUBLICATIONS

J. Fitchen et al., "Plant Virus Expressing Hybrid Coat Protein With Added Murine Epitope Elicits Autoantibody Response", Vaccine, vol. 13, pp. 1051–1057 (1996).

Baer et al. EMBO J. vol. 13, No. 3, 1994, pp. 727–735.

Donson et al. PNAS USA, vol. 88, Aug. 1991, pp. 7204–7208.

G. Porta et al., Development of Cowpea Mosaic Virus as a High–Yielding System for the Presentation of Foreign Peptides, *Virology* vol. 202, 949–955 (1994).

T.H. Turpen et al., Malarial Epitopes Expressed on the Surface of Recombinant Tobacco Mosaic Virus; *Bio/Technology*, vol. 13, 53–57 (1995).

L. McLain et al., Human Immunodeficiency Virus Type 1–Neutralizing Antibodies Raised to a Glycoprotein 41 Peptide Expressed on the Surface of a Plan Virus; *Aids Res. and Human Retroviruses*, vol. 11, 327–334, (1995).

J. Fitchen et al. Plant Virus Expressing Hybrid Coat Protein With Added Murine Epitope Elicits Autoantibody Response; *Vaccine*, vol. 13, 1051–1057 (1995).

R. Usha et al., Expression of an Animal Virus Antigenic Site on the Surface of a Plant Virus Particle; *Virology*, vol. 197, 366–374 (1993).

Vidadi Yusibov and Sue Loesch–Fries, High Affinity RNA–Binding Domains of Alfalfa Mosaic Virus Coat Protein Are Not Required for Coat Protein–Mediated Resistance; *Proc. National Academy of Science. U.S.*, vol. 92, 8980–8984 (1995).

Vidadi Yusibov, et al., Purification, Characterization, Assembly and Crystallization of Assembled Alfalfa Mosaic Virus Coat Protein Expressed in *Escherichia Coli*, *J. Gen. Virol*, vol. 77, 567–573 (1996).

*Primary Examiner*—Jeffrey Stucker
*Assistant Examiner*—Phuong T. Bui
*Attorney, Agent, or Firm*—Volpe and Koenig, PC

[57] ABSTRACT

A fusion capsid protein comprising a plant virus capsid protein fused to an antigenic polypeptide is used as a molecule for presentation of that polypeptide to the immune system of an animal such as a human. The plant virus capsid protein is that of an alfalfa mosaic virus (AlMV) or ilarvirus.

12 Claims, 9 Drawing Sheets

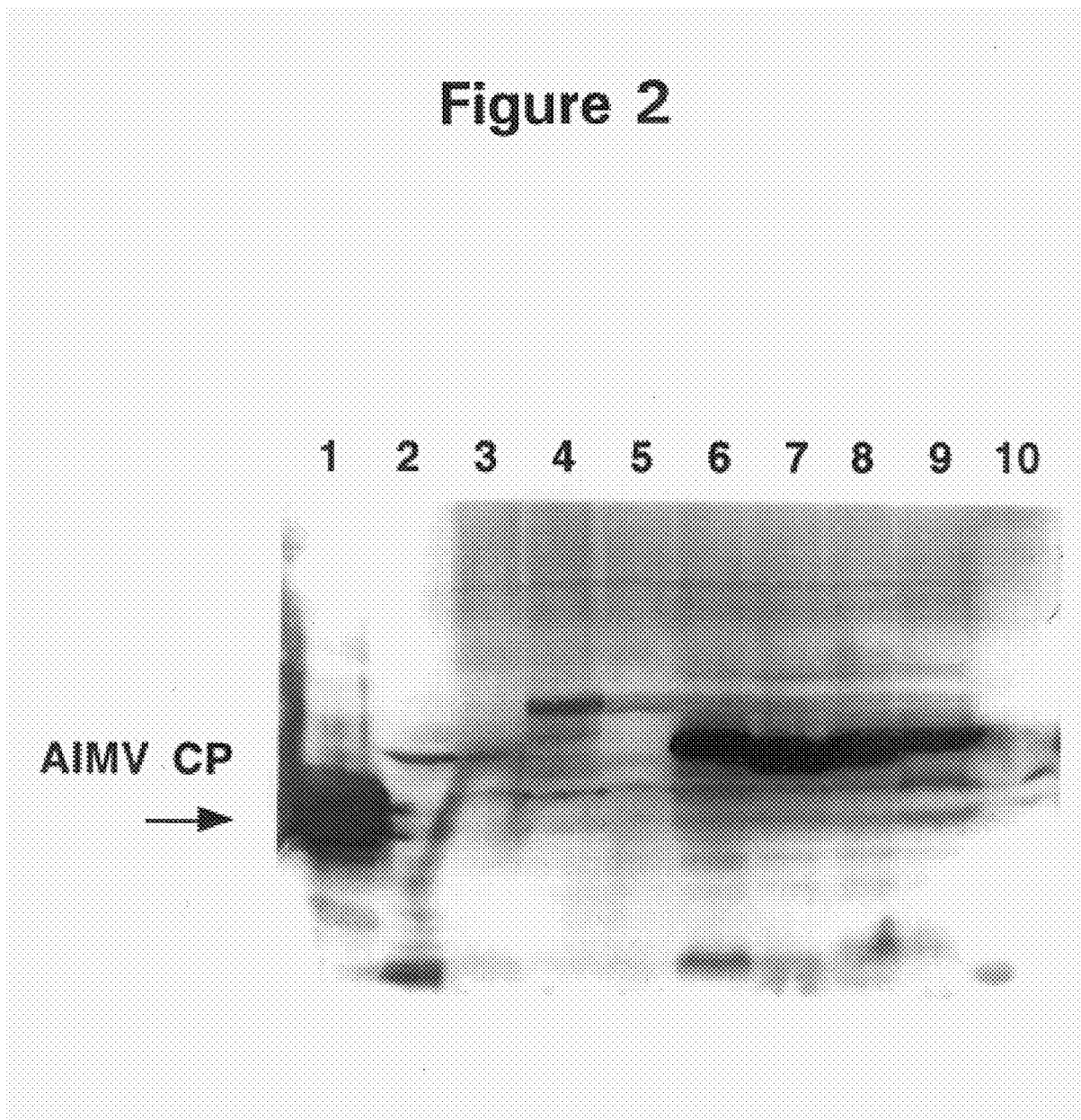

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 35 amino acids
       (B) TYPE: amino acid
       (D) TOPOLOGY:linear (iii) HYPOTHETICAL: N (xi) SEQUENCE DESCRIPTION: SEQ ID NO:1:

Cys Thr Arg Pro Asp Tyr Asp Lys Arg Lys Arg Ile His Ile Gly Pro
1               5                   10                  15

Gly Arg Ala Phe Tyr Thr Thr Lys Asp Ile Ile Gly Thr Ile Arg Gln
            20                  25                  30

Ala His Cys
        35

(2) INFORMATION FOR SEQ ID NO:2:

(i) SEQUENCE CHARACTERISTICS:
       (A) LENGTH: 36 amino acids
       (B) TYPE: amino acid
       (D) TOPOLOGY: linear (iii) HYPOTHETICAL: N (xi) SEQUENCE DESCRIPTION: SEQ ID NO:2:

Cys Thr Arg Pro Asp Asp Asp Thr Arg Lys Ser Ile Arg Ile Gln Arg
1               5                   10                  15

```
Gly Pro Gly Arg Ala Phe Val Thr Ile Gly Lys Ile Gly Asp Met Arg
            20                  25                  30

Gln Ala His Cys
        35
```

(2) INFORMATION FOR SEQ ID NO:3:

(i) SEQUENCE CHARACTERISTICS:
        (A) LENGTH: 34 amino acids
        (B) TYPE: amino acid
        (D) TOPOLOGY: linear (iii) HYPOTHETICAL: N (xi) SEQUENCE DESCRIPTION: SEQ ID NO:3:

```
Met Ser Ala Val Tyr Thr Arg Ile Met Met Asp Gly Gly Arg Leu Lys
1               5                   10                  15

Arg Tyr Glu Ala Ala Glu Leu Thr Leu Thr Asp Val Ala Leu Ala Asp
            20                  25                  30

Asp Ser
```

(2) INFORMATION FOR SEQ ID NO:4:

(i) SEQUENCE CHARACTERISTICS:
        (A) LENGTH:    38 amino acids
        (B) TYPE:      amino acid
        (D) TOPOLOGY:  linear (iii) HYPOTHETICAL: N (xi) SEQUENCE DESCRIPTION: SEQ ID NO:4:

```
Met Ser Ala Val Tyr Thr Arg Ile Met Met Asp Gly Gly Arg Leu Lys
1               5                   10                  15

Arg Pro Pro Asp Gln Leu Val Ala Leu His Asp Gly Ile Glu Lys Leu
            20                  25                  30

Val Val Glu Glu Asp Ser
        35
```

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (iii) HYPOTHETICAL:N (xi) SEQUENCE DESCRIPTION: SEQ ID NO:5:

AGA TCT CGA GAT GAG TTC ATC TGT AGA AAT TAA TTG TAC A    40

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (iii) HYPOTHETICAL:N (xi) SEQUENCE DESCRIPTION: SEQ ID NO:6:

CGG CTC GAG CTA CTA ATG TTA CAA TG    26

(2) INFORMATION FOR SEQ ID NO:7:

```
        (i) SEQUENCE CHARACTERISTICS:
            (A) LENGTH: 27 base pairs
            (B) TYPE: nucleic acid
            (C) STRANDEDNESS: single
            (D) TOPOLOGY: linear (iii) HYPOTHETICAL: N (xi) SEQUENCE DESCRIPTION: SEQ ID NO:7:

GCA CTC GAG CAG ATG GAA CAA GCC CCA                                          27

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (iii) HYPOTHETICAL: N (xi) SEQUENCE DESCRIPTION: SEQ ID NO:8:

GCA CTC GAG GCG GAT CTA ATG GCT CCA TT                                       29

(2) INFORMATION FOR SEQ ID NO:9:

(i) SEQUENCE CHARACTERISTICS:
            (A) LENGTH:30 base pairs
            (B) TYPE:nucleic acid
            (C) STRANDEDNESS: single
            (D) TOPOLOGY:linear (iii) HYPOTHETICAL:     N (xi) SEQUENCE DESCRIPTION:SEQ ID NO:9:

GCA CTC GAG GTG ATG CAA CCT ATA ATA GTA                                      30

(2) INFORMATION FOR SEQ ID NO:10:

(i) SEQUENCE CHARACTERISTICS:
            (A) LENGTH: 29 base pairs
            (B) TYPE: nucleic acid
            (C) STRANDEDNESS: single
            (D) TOPOLOGY:linear (iii) HYPOTHETICAL: N (xi) SEQUENCE DESCRIPTION: SEQ ID NO:10:

GCA CTC GAG GCC AGA TCA TCA ATA TCC CA                                       29

(2) INFORMATION FOR SEQ ID NO:11:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (iii) HYPOTHETICAL: N (xi) SEQUENCE DESCRIPTION: SEQ ID NO:11:

GCGCTCGAGA TGTCCGCCGT CTACACCCGA ATTATGATGA                                  40

ACGGAGGACG ACTTAAGCGA TACGAGGCAG CTGAAC                                      76

(2) INFORMATION FOR SEQ ID NO:12:

(i) SEQUENCE CHARACTERISTICS:
```

(A) LENGTH: 71 base pairs
        (B) TYPE: nucleic acid
        (C) STRANDEDNESS: single
        (D) TOPOLOGY: linear (iii) HYPOTHETICAL: N (xi) SEQUENCE DESCRIPTION: SEQ ID NO:12:

GCGCTCGAGT CGTCTGCTAG TGCCACGTCG GTAAGGGTAA                                40

GTTCAGCTGC CTCGTATCGC TTAAGTCGTC C                                        71

(2) INFORMATION FOR SEQ ID NO:13:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (iii) HYPOTHETICAL: N (xi) SEQUENCE DESCRIPTION: SEQ ID NO:13:

GCGCTCGAGA TGTCCGCCGT CTACACCCGA ATTATGATGA                                40

ACGGAGGACG ACTTAAGCGA CCACCAGACC AGCTTG                                   76

(2) INFORMATION FOR SEQ ID NO:14:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (iii) HYPOTHETICAL:N (xi) SEQUENCE DESCRIPTION: SEQ ID NO:14:

GCGCTCGAGT CCTCTTCCAC CACAAGGTGC TCATTTTCGT                                40

CGTGAAGGTT CACAAGCTGG TCTGGTGGTC GCTTAAGTCG                                80

TCC                                                                       83

(2) INFORMATION FOR SEQ ID NO:15:

(i) SEQUENCE CHARACTERISTICS:
        (A) LENGTH:96 amino acids
        (B) TYPE: amino acid
        (D) TOPOLOGY:linear (iii) HYPOTHETICAL:N (xi) SEQUENCE DESCRIPTION: SEQ ID NO:15:

Met Glu Gln Ala Pro Glu Asp Gln Gly Pro Gln Arg Glu Pro Tyr Asp
1               5                   10                  15

Glu Trp Thr Leu Glu Leu Leu Glu Glu Leu Lys Ser Glu Ala Val Arg
            20                  25                  30

His Phe Pro Arg Ile Trp Leu His Asp Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Arg Gln Arg Arg Ala Arg Asp Gly Ala Ser Arg Ser
                85                  90                  95

```
(2) INFORMATION FOR SEQ ID NO:16:

(i) SEQUENCE CHARACTERISTICS:
        (A) LENGTH: 81 amino acids
        (B) TYPE: amino acid
        (D) TOPOLOGY: linear (iii) HYPOTHETICAL: N (xi) SEQUENCE DESCRIPTION: SEQ ID NO:16:

Met Glu Pro Ile Ile Val Ala Ile Val Ala Leu Val Val Ala Ile Ile
1               5                   10                  15

Ile Ala Ile Val Val Trp Ser Ile Val Ile Ile Glu Tyr Arg Lys Ile
                20              25                  30

Leu Arg Gln Arg Lys Ile Asp Arg Leu Ile Asp Arg Leu Ile Glu Arg
            35              40                  45

Ala Glu Asp Ser Gly Asp Glu Ser Glu Gly Glu Val Ser Ala Leu Val
        50                  55                  60

Glu Met Gly Val Glu Met Gly His His Ala Pro Trp Asp Ile Asp Asp
65                  70              75                  80

Leu
```

POLYPEPTIDES FUSED WITH ALFALFA MOSAIC VIRUS OR ILARVIRUS CAPSID PROTEINS

FIELD OF THE INVENTION

The field of the invention is recombinant plant viruses, especially their use as immunizing agents which carry antigenic sequences from mammalian (e.g., human) or other animal pathogens and their use as a system for increased production of polypeptides of interest.

BACKGROUND

Traditionally, successful vaccination has been dependent upon the use of live attenuated viruses or preparations of killed pathogenic organisms. These vaccines are very effective in controlling or, as in the case of smallpox, even eliminating certain infectious diseases. However, their use often present safety concerns. Subunit vaccines based on peptide or proteins derived from a pathogen are less hazardous than traditional vaccines but have generally suffered from poor immunogenicity and high expense. Moreover, current vaccines with a few exceptions must be administered parenterally. However, it is well known that most pathogens gain entry across the mucosal surfaces of the body and a mucosal immune response would therefore be more appropriate.

Both safety concerns and the desire to target mucosal tissues for more effective immunization against common pathogens dictate the need for new approaches to vaccination. For induction of a mucosal response, oral administration of antigen is appropriate, inexpensive, and safe. However, in order to efficiently immunize by the oral route, several obstacles such as degradation from low pH or proteases in the gastrointestinal GI tract, the short exposure to immune induction sites, and limited permeability must be overcome.

Recent studies demonstrate that plants and plant viruses can function as effective tools for vaccine production and delivery. Furthermore, like liposomes and microcapsules, it is expected that plant cells and plant viruses will serve as delivery vehicles providing natural protection for the antigen associated with them and enhancing the uptake of the antigen from the GI tract. Such new developing "green system vaccines" have significant advantages over the traditional and synthetic vaccines as regards safety, deliverability via either parenteral, nasal or oral routes, and lower cost of production.

BRIEF SUMMARY OF THE INVENTION

In one general aspect, the current invention is a process of delivering a fusion capsid protein (a plant virus capsid protein fused to a foreign polypeptide) to a mammal (such as a human) or other animal using recombinant tobacco mosaic virus (TMV) genetic material (TMV genetic material combined with genetic material that codes for a chimeric capsid protein, the chimeric capsid protein being capsid protein of either an alfalfa mosaic virus (AlMV) capsid protein (CP) or ilarvirus CP, fused to the foreign polypeptide) as a delivery vehicle to that mammal or other animal. A foreign polypeptide is one that does not naturally occur in either TMV, an AlMV or an ilarvirus. The fusion protein is administered to the mammal or other animal for purposes of inducing an immune response against the foreign polypeptide. In a second general aspect, the invention is a production process: the use of such a chimeric virus to express the fused coat protein (comprising either an antigenic or nonantigenic foreign protein) in a plant.

The "pep" polypeptide has the following amino sequence:

```
For BrzCPMNV3:     CTRPNYNKRKRIHIGPGRAFYTTKNIIGTIRQAHC               (SEQ ID NO:1)

For BRzCPNLV3:     CTRPNNNTRKSIRIQRGPGRAFVTIGKIGNMRQAHC              (SEQ ID NO:2)

For BRzCPDnv10c:   MSAVYTRIMMNGGRLKRYEAAAELTLTDVALADDS               (SEQ ID NO:3)

For BRzCPDrg24:    MSAVYTRIMMNGGRLKRPPDQLVALHDGIEKLVVEEDS            (SEQ ID NO:4)

For BRzCPNLVpr:                                                      (SEQ ID NO:15)

HIV-1 NL 4.3 Vpr-

MEQAPEDQGPQREPYNEWTLELLEELKSEAVRHFPRIWLHNLGQHIYETYGDTWAGVEAIIRILQQLLFIHF

RIGCRHSRIGVTRQRRARNGASRS

For BRzCPNLVpu:                                                      (SEQ ID NO:16)

HIV-1 NL 4.3 Vpu-

MQPIIVAIVALVVAIIIAIVVWSIVIIEYRKILRQRKIDRLIDRLIERAEDSGNESEGEVSALVEMGVEMGH

HAPWDIDDL
```

FIG. 2. Accumulation of chimeric AlMV CP, fused with different peptides, in tobacco protoplasts infected with transcripts of recombinant virus. Proteins were separated by electrophoresis in a 13% SDS-polyacrylamide gel and electroblotted on nylon membrane. The proteins were reacted with monoclonal antibodies to AlMV CP followed by detection with Westatin immunostain kit (Sigma). Lane 1 represents wt AlMV CP. Lane 2 and 3 are in vitro translation products of pSPCPD10c and pSPCPDrg24, respectively. Lane 4—pBRzCPNLVpu, lane 5—pBRzCPNLVpr, lane 6—pBRzCPDrg24, lane 7—pBRzCPDNV10c, lane 8—pBRzCPMNV3, lane 9—pBRzCPNLV3, and lane 10—B30Rz.

Figure 3A:
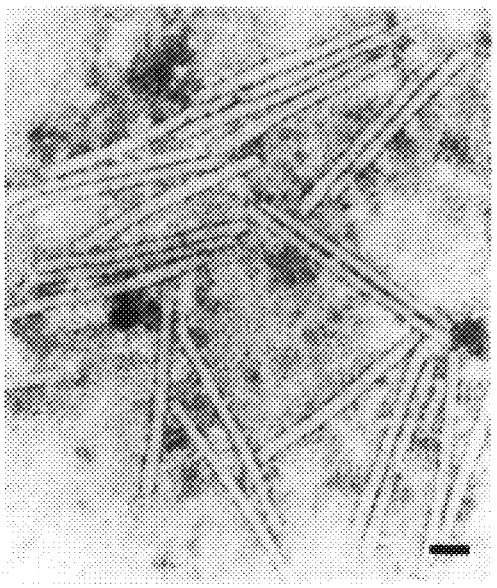
Figure 3B:
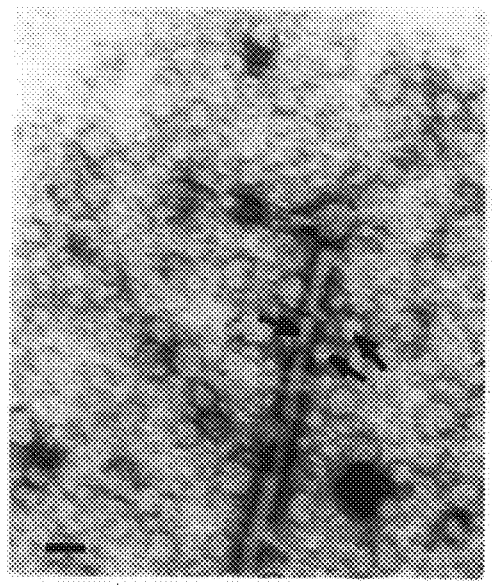

FIGS. 3A and 3B. Electron micrographs of recombinant AlMV particles from tobacco plants, infected with recombinant transcripts of TMV presenting different constructs. The particles were negatively stained with 2% of uranyl acetate. The bars indicate 100 nm. A—B30Rz. B—pBRzCPNLV3. The single arrow indicates a TMV particle. The double arrow indicates indicates recombinant AlLMV particles.

Figure 4:
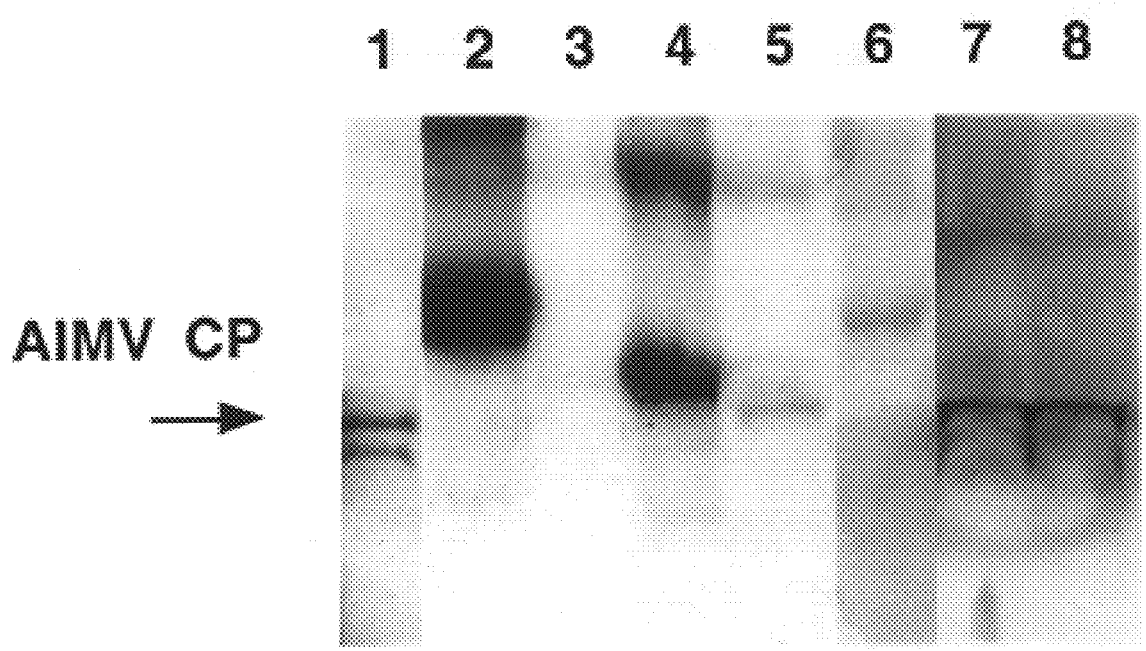

FIG. 4. Accumulation of chimeric AlMV CP in systemically infected tobacco leaves. The tobacco leaves were inoculated with transcripts of recombinant virus. Proteins were separated by electrophoresis in a 13% SDS-polyacrilamide gel. The proteins were reacted with monoclonal antibodies to AlMV CP followed by detection with Westatin immunostain kit. Lane 1 represents wt AlMV CP. Two—pBRzCPNLVpu, 3—B30Rz, 4—pBRzCPDrg24, 5—pBRzCPDNV10c, 6—pBRzCPNLVpr, 7—pBRzCPMNV3, and 8—pBRzCPNLV3.

Figure 5:
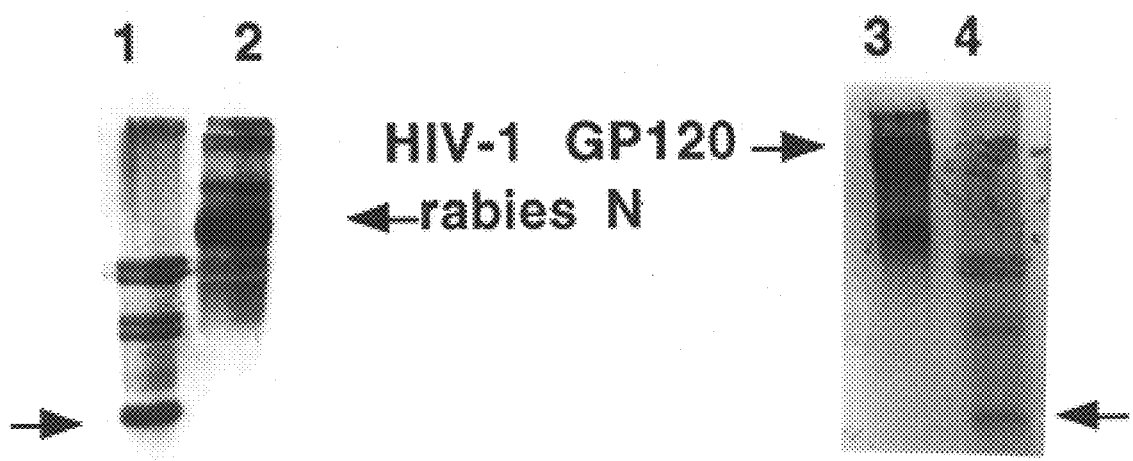

FIG. 5. Immunoprecipitation of chimeric particles containing rabies and HIV-1 epitopes. The particles purified from plant tissue which were coinfected with transcripts of recombinant virus and immunoprecipitated using monoclonal antibodies to the linear epitop of rabies G protein (rg24). Immunoprecipitated proteins were separated by electrophoresis in a 13% SDS-polyacrilamide gel. The proteins were reacted with antibodies to HIV-1 V3 loop or with monoclonal antibodies to N protein of rabies followed by detection with Westatin immunostain kit. Lane 1 represents immunoprecipitated proteins reacting with antibodies to N protein. Two—wild type rabies. 3—HIV-1 gp120 reacted with antibodies to V3 loop, and 4—immunoprecipitated proteins reacting with antibodies to V3 loop.

Figure 6A:
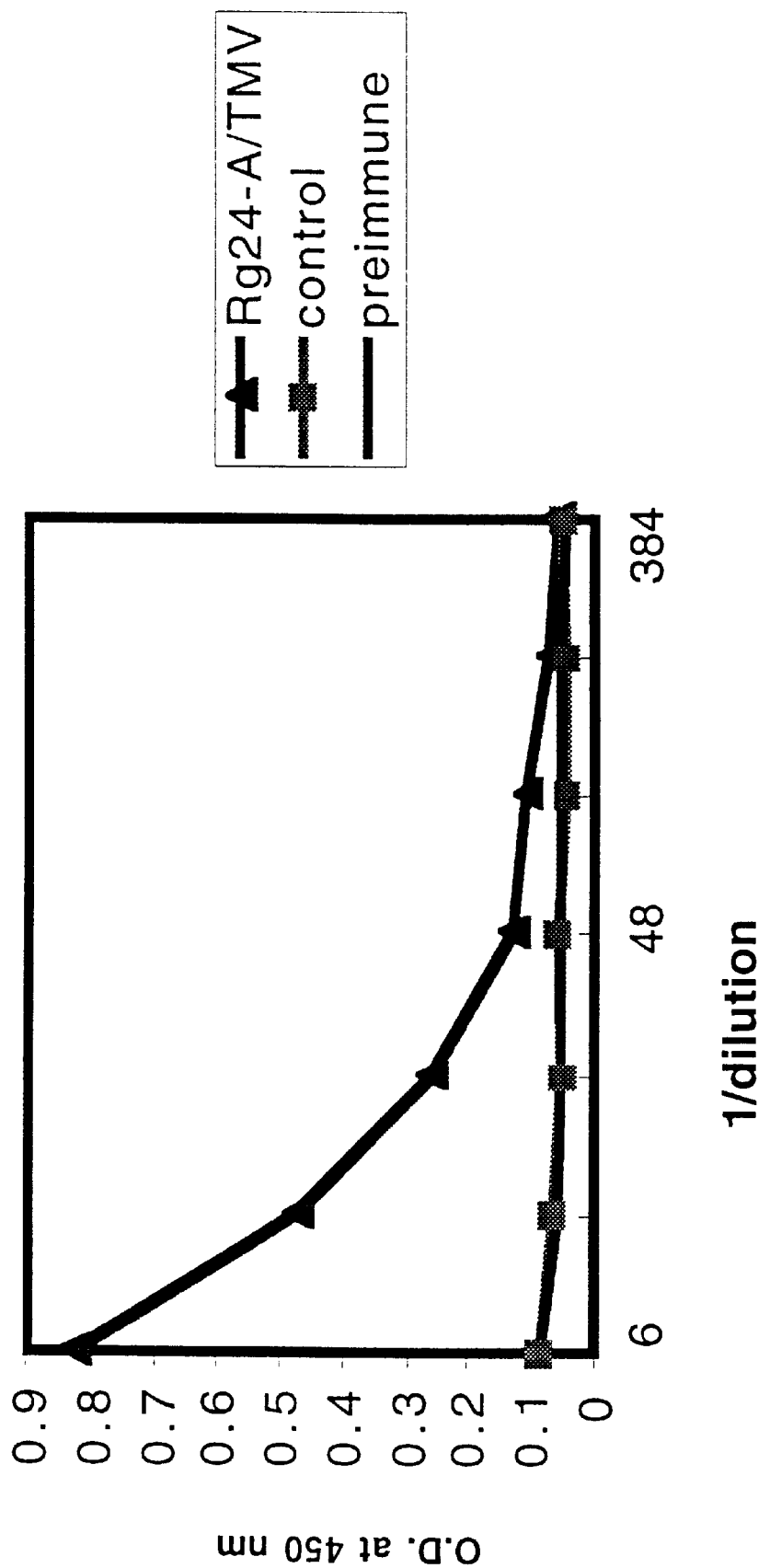
Figure 6B:
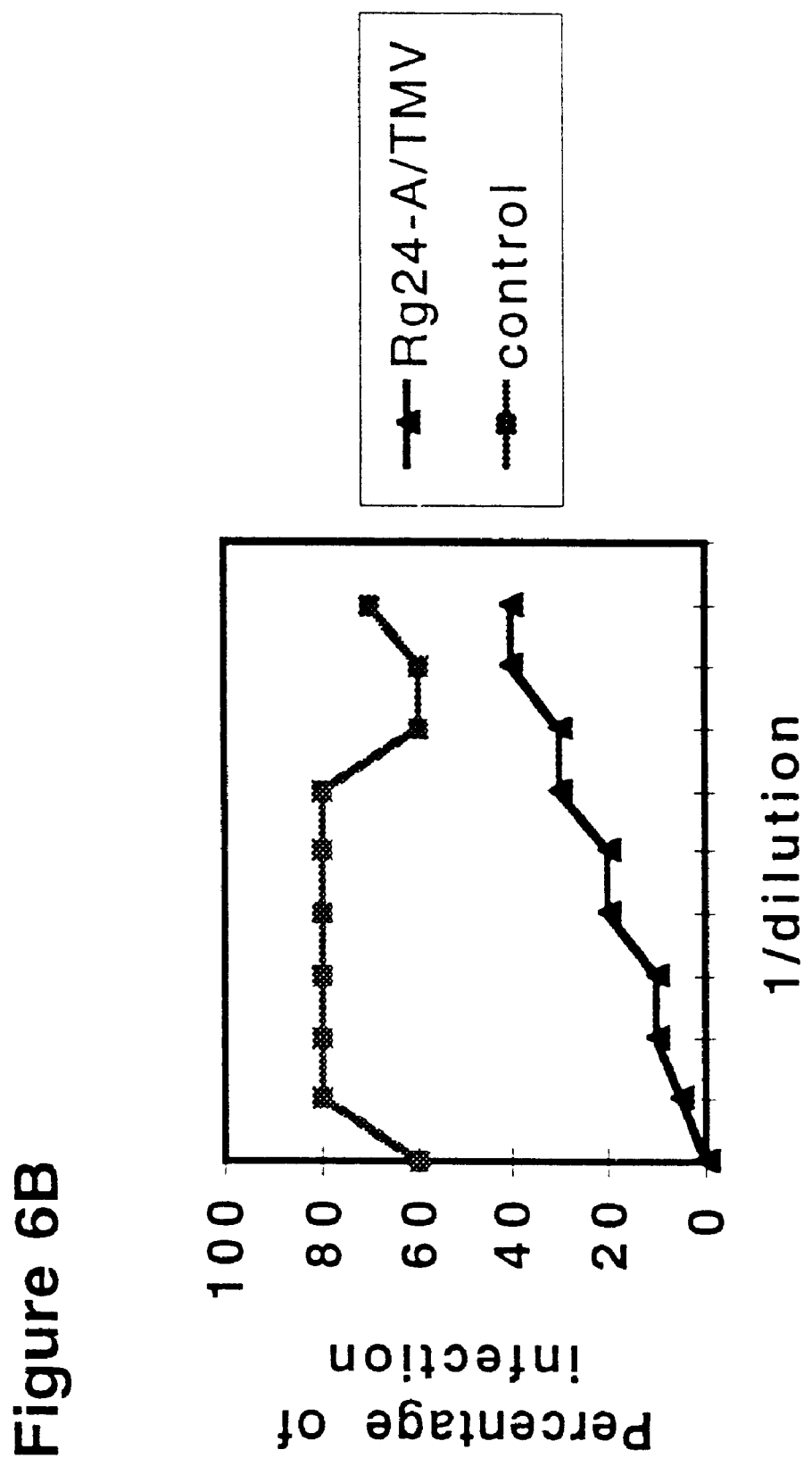

FIGS. 6A and 6B. Results obtained in ELISA and neutralization assay as a comparison of control mouse immunized with mix of TMV and AlMV and mouse immunized with pBRzCPDrg24. Eight-week-old female Swiss-Webster outbred mice were immunized with 10-ug doses of each recombinant virus engineered to express the epitopes. Three immunizations of 0.1 mL were administered intraperitoneally at 2-week intervals with complete Freund's adjuvant at a 1:1 (v:v) ratio. An equal quantity of a mixture of wild type TMV plus AlMV was used with complete Freund's adjuvant as a control. Ten to 14 days after each immunization, serum samples were obtained from individual mice, and specific antibody titers for rabies virus were assessed using a solid-phase enzyme-linked immunosorbent assay. Assay results are expressed in O.D. units. Specific neutralization of rabies CVS-11 virus was assessed in a modified rapid fluorescent focus-forming assay using serum from pBRzCPDrg24-immunized mice and BHK indicator cells. One out of five mice had neutralizing antibodies.

Figure 7:
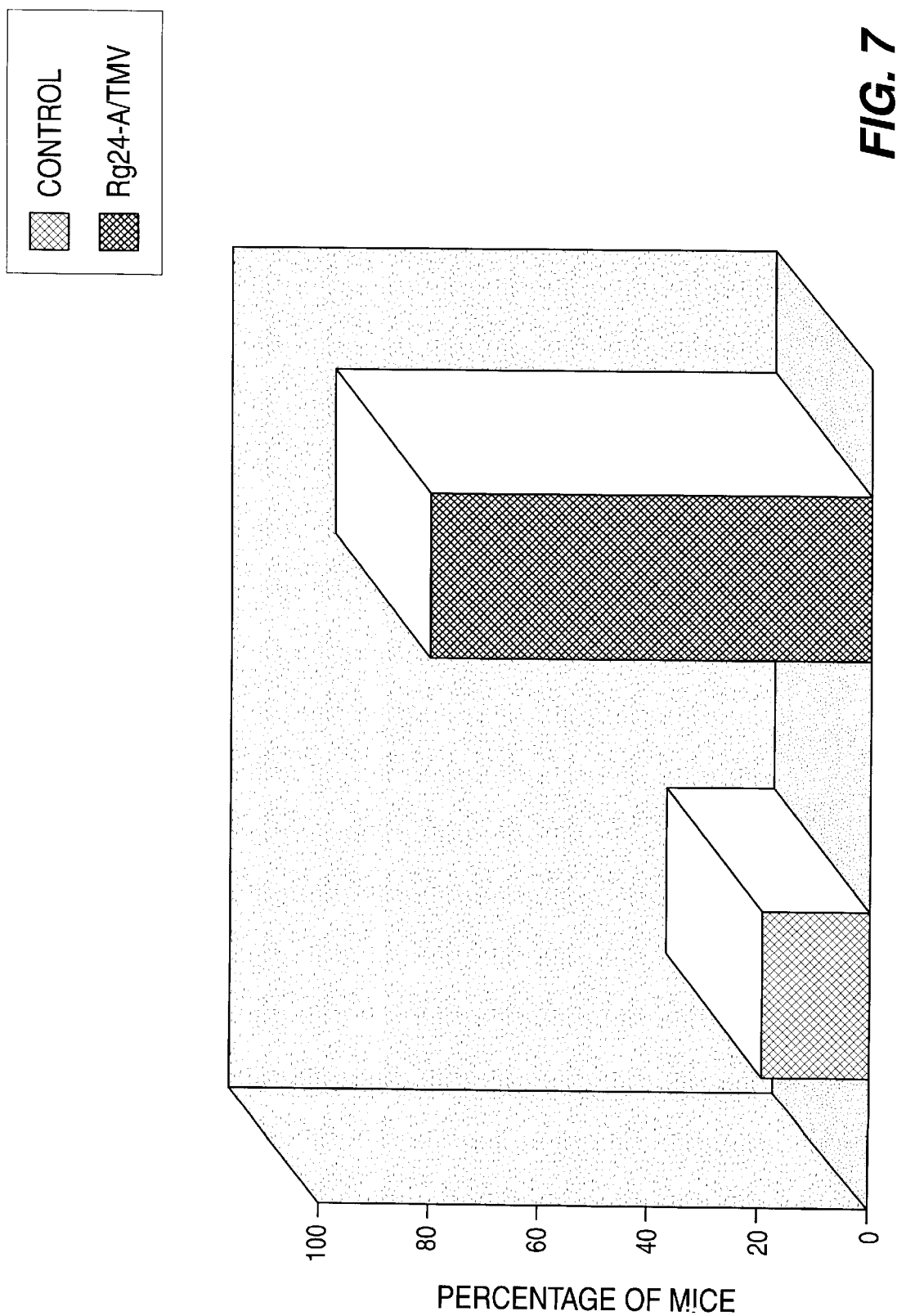

FIG. 7. The percentage of mice producing specific rabies virus antibodyes after I.p. immunization with pBRzCP-Drg24 (Rg24-A/TMV) or mix of AlMV plus TMV (Control). The results were obtained in ELISA. Experiment is described in the legend to FIG. 6.

DETAILED DESCRIPTION

Glossary and Discussion of Terms Used

A "plant" for purposes of this patent application includes liverworts (Hepaticae), mosses (Musci), psilopsids (Psilopsida), club mosses (Lycopsida), horsetails (Sphenopsida), ferns and seed plants, and certain fungi specified below, and algae including blue-green algae. Ferns and seed plants together make up the Pteropsida. Seed plants include gymnosperms (Gymnospermae) and angiosperms (Angiospermae). The great majority of plants used for food are angiosperms. For purposes of this application, the following fungi are considered plants: Basidiomycetes, which include mushrooms. The following are not considered plants for purposes of this application: bacteria, single-celled eukaryotes, and the following fungi: Phycomycetes, Ascomycetes (yeasts), and Deuteromycetes.

The term "plant tissue" includes any tissue of a plant. Included are whole plants, any part of plants, plant cells, plants seeds, and plant protoplasts.

The word "animal" refers to humans as well as other animals.

A "bird" is a warm-blooded vertebrate of the class Aves.

A "fish" is a cold-blooded aquatic vertebrate, having gills and fins.

A "chimeric protein" is created when two or more genes that normally code for two separate proteins recombine, either naturally or as the result of human intervention, to code for a protein that is a combination of all or part of each of those two proteins.

The phrase "code for" is used in this application to refer to both the nucleic acid sequence that codes for a polypeptide sequence and a base sequence complementary to such a nucleic acid sequence.

A "fusion capsid protein" is a chimeric protein in which one of the genes in the chimera codes for a plant virus capsid protein.

A "bipartite fusion capsid protein" is a fusion wherein genes for two proteins recombine.

A "tripartite fusion capsid protein" is a fusion wherein genes for three proteins recombine.

A "pathogen protein" is a protein that is coded for by the genetic material of a pathogen.

A "naturally occurring plant protein" is one that is normally found in a plant, at least one stage in its life cycle, in its natural habitat.

"Infecting a plant cell" means infecting a plant cell with one or more genes that it does not naturally have, the infection being by a nucleic acid molecule that may or may not be encapsidated within a virus.

"Protective immunity" is the ability of an animal, such as a mammal, bird, or fish, to resist (delayed onset of symptoms or reduced severity of symptoms), as the result of its exposure to the antigen of a pathogen, disease or death that otherwise follows contact with the pathogen. Protective immunity is achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Mucosal immunity can be stimulated by an oral vaccine. The primary result of protective immunity is the destruction of the pathogen or inhibition of its ability to replicate itself.

"Humoral immunity" is the result of IgG antibodies and IgM antibodies in serum.

"Cellular immunity" can be achieved through cytotoxic T lymphocytes or through delayed-type hypersensitivity that involves macrophages and T lymphocytes, as well as other mechanisms involving T cells without a requirement for antibodies.

A "derivative cell" derived from an infected plant cell is one created as a result of the infected plant cell undergoing cell division or a series of cell divisions such that one or more copies of the foreign gene introduced into the plant cell by infection is in the derivative cell.

"Ilarviruses" include, but are not limited to the following subgroups: tobacco streak virus, prune dwarf virus, lilac ring mottle virus, citrus leaf rugose virus, citrus variegation virus, elm mottle virus, spinach latent virus, asparagus virus 2, Parietaria mottle virus, hydrangea mosaic virus, apple mosaic virus, and Prunus necrotic ringspot virus.

A "recombinant virus" is one in which the genetic material of a virus has combined with other genetic material.

A "polypeptide" is a molecule in which there is at least four amino acids linked by peptide bonds.

"Viral nucleic acid" may be the genome (or the majority thereof) of a virus, or a nucleic acid molecule complementary in base sequence to that genome. A DNA molecule that is complementary to viral RNA is also considered viral nucleic acid. An RNA molecule that is complementary in base sequence to viral DNA is also considered to be viral nucleic acid.

"AlMV" is alfalfa mosaic virus.

"TMV" is tobacco mosaic virus.

A "vaccine" in the present invention is the fusion capsid protein, any particle of which that protein is part, or any preparation such as plant material of which that protein is part.

"Plurality" means more than one.

ASPECTS OF THE INVENTION

In a general aspect, the invention is a process of administering a polypeptide to an animal (especially a mammal, bird, or fish), the process comprising the steps of:

(1) infecting a plant cell with recombinant plant virus nucleic acid that will be processed in the plant cell to produce a fusion capsid protein comprising virus capsid protein and a polypeptide that is not a plant virus capsid protein, said virus capsid protein being an AlMV coat protein or ilarvirus capsid protein, thereby creating a infected cell;

(2) cultivating the infected cell, or a derivative cell derived from said infected cell, under conditions where said infected cell or derivative cell makes the fusion capsid protein; and (3) administering the fusion capsid protein or a portion thereof to an animal.

In step (1) the viral nucleic acid may either be in a virus or not in a virus. If it is not in a virus, it may either be pure nucleic acid or nucleic acid associated with other molecules or molecular structures.

In step (1) if the recombinant plant virus nucleic acid comprises TMV nucleic acid, the TMV nucleic acid will preferably comprise nucleic acid coding for the TMV 123 kDA 183 kDa, and 30 kDa proteins.

In steps (1) and (2), the infected cell or derivative cell may either be part of a plant or plant tissue or may be free of other plant cells.

In step (1), it is preferable that the viral nucleic acid have sufficient genetic information to produce viral particles during step (2).

The route of administration in step (3) can be parenteral or nonparenteral. If administered parenterally, the protein to be administered to the animal will preferably be substantially pure of other material found in the plant cells that produced it.

In step (3), the protein or portion thereof may be in or part of the infected or derivative cell, part of an extract of such a infected or derivative cell or, as a result of protein purification, free of other material normally present in the infected or derivative cell.

The result of step (3) is, in a particular embodiment of the invention, an immune response against the part of the fusion capsid protein that is not plant viral protein. That immune response preferably results in either protective immunity or systemic tolerance.

The steps for purifying a fusion capsid protein are ones commonly used for the fractionation of plants into their protein components and the separation of individual proteins from other components of the infected or derivative cell. Such steps include protection of the native conformation of the pathogen protein by steps such as flash freezing the plant material with dry ice or liquid nitrogen.

An extract would be created by a process comprising mechanical or chemical disruption of a cell. In some cases, additional protein purification steps would be used to make the extract.

In one important embodiment of the invention, in step (3) the fusion capsid protein is in part of a plant or plant product and is fed to the mammal (i.e. oral route of administration). In such a case, it is preferable that the plant is raw; i.e., has not been cooked (heated above the temperatures associated with growth, storage, and transport). In the examples described below, the plant is not cooked. Animals typically may eat the plant, pieces of the plant, a puree from the plant, or plant juice. As a result, it is frequently preferred that step (2) takes place in an edible plant or part of an edible plant.

Animals vary as regards which food is edible. Plants of greatest interest include potatoes, tomatoes, peas, beans, alfalfa, citrus fruits (e.g., oranges, lemons, grapefruit), grapes, carrots, strawberries, blueberries and other berries, bananas, rice, wheat, corn, barley, oats, rye, dates, cabbage, Brussel sprouts, cauliflower, turnips, cucurbits, papaya, guava, apples, cherries, apricots, pears, and grapes.

In another important embodiment of the invention, the fusion capsid protein of interest is extracted in purified form from the plant and administered as a substantially pure protein, possibly with an adjuvant or other compounds needed to facilitate or improve vaccine administration.

As in the case of the rabies virus glycoprotein (Rgp), the polypeptide referred to in step (1) may be one that is a glycoprotein in the pathogen.

Pathogens of interest

A pathogen is any organism such as a virus, bacterium, fungus, or parasite, as well as a protein which is capable of self-replication such as a prion and capable of inducing disease in an animal.

Pathogens against which vaccines created by the present invention are effective are those including but not limited to bacteria of the genera streptococci and staphylococci, as well as the mycoplasma, rickettsia and spirochetes. The following viral groups of the parvoviridae, papovaviridae, adenoviridae, herpesviridae, poxviridae, iridoviridae, picornaviridae, caliciviridae, togaviridae, flaviviridae, coronaviridae, ortho- and paramyxoviridae, rhabdoviridae, bunyaviridae, reoviridae, birnaviridae, and the retroviruses all contain representative members with application for vaccines of the present invention.

Pathogens against which vaccines of the present invention are expected to be particularly useful are rabies, respiratory syncytial virus, cholera, typhoid fever, herpes simplex types I and II, tuberculosis, pathogenic pneumococci, human immunodeficiency virus-1 (HIV-1) and human immunodeficiency virus-2 (HIV-2). The spectrum of pathogens includes those of veterinary significance and includes parvoviridae, papovaviridae, adenoviridae, herpesviridae, poxviridae, iridoviridae, picornaviridae, caliciviridae, togaviridae, flaviviridae, coronaviridae, ortho- and paramyxoviridae, rhabdoviridae, bunyaviridae, reoviridae, birnaviridae, and the retroviruses. Both gram negative and gram positive bacteria and spirochetes are also expected to be pathogens which may be clinically affected by the plant vaccines of the present invention.

Methods for infecting plants

Genes may be transferred by any of a variety of infection means, which means include but are not limited to:

1) Coating a plant surface with viruses or viral nucleic acid, possibly one that has undergone abrasion;

2) Microparticle bombardment, for example as described for wheat by V. Vasil et al., *Bio/Technology* 9, 743 (1991) and generally in *Bio/Technology* 10, 286 (1992).

3) Electroporation, for example as described for lettuce by M. C. Chupeau et al., *Bio/Technology* 7, 503 (1989).

4) Liposome fusion with protoplasts (A. Deshayes et all., *EMBO J.* 4, p2731–2737 (1985)).

5) Polyethylene glycol-mediated transformation (I. Potrykus et al., *Mol. Gen Genetics,* 197, 183–188).

6) Microinjection (R. Griesbach, Biotechnology 3, p348–350; C. K. Shewmaker *Mol. Gen. Genetics,* 202 p. 179–185 (1986)).

It may be desirable to target protein expression to different plant tissues (i.e. fruit and leaves) and to different intracellular locations (i.e. chloroplast, vacuole, plasma membrane) in order to enhance protection of the recombinant protein. It may also be desirable to present the antigen as part of larger structure for uptake by the M cells of the Peyers patch.

It may be desirable to combine presentation of the primary antigens with a biologically active molecule that will stimulate and or enhance an immune response and serve as an adjuvant. Since modified plants can be crossed genetically, plants expressing an adjuvant protein and a primary antigen can be produced separately and combined to deliver antigen and adjuvant in one plant.

Plant viruses

The quasi-isometric/bacilliform viruses can, according to J. A. Levy et al. (*Virology,* 3rd edition, Prentice Hall, Englewood Cliffs, N.J. (1994)), be divided into two subgroups: AlMV and the ilarviruses. The antigen-presenting capsid protein in the present invention is that of a quasi/bacilliform virus: its synthesis is driven by a genome constructed to produce a chimeric capsid protein whose components include the quasi/bacilliform capsid protein and the antigenic protein or polypeptide of interest. The virus that delivers the chimeric capsid protein to a plant for production of the antigenic protein may itself be a quasi-isometric/bacilliform virus, or alternatively, may be a nonenveloped virus with a positive-sense RNA genome that is not a quasi-isometric/bacilliform virus. Below, examples are given of how AlMV or TMV can form the major part of the delivery vehicle.

Tobacco mosaic virus and alfalfa mosaic virus

Two viruses used herein to exemplify the invention are tobacco mosaic virus (TMV) and alfalfa mosaic virus (AlMV). TMV is the type member of the tobamovirus group. TMV consists of a single plus-sense genomic RNA (6.5 kb) encapsidated with a unique coat protein (17.5 kDa) which results in rod-shaped particles (300 nm). A wide host range of tobacco mosaic virus allows one to use a variety of plant species as production and delivery systems. The expression of protein depends only upon virus replication and does not interfere with plant nuclear transcription machinery thus providing high levels of protein accumulation in infected cells. It has been shown that foreign genes inserted into this vector can produce high levels of protein (Yusibov et al., *Proc. Natl. Acad. Sci. U.S.* 92, 8980 (1995)). The second component of a recombinant expression vector exemplified herein is AlMV CP. AlMV is a type member of Bromoviridae family. The genome of this virus consists of three positive-sense RNAs (RNAs 1–3) which are encapsidated by CP (24 kDa) resulting in a 30–60 nm bacilliform particle. The fourth RNA (subgenomic RNA4) of AlMV is the messenger for CP and is synthesized from genomic RNA3. RNA4 is separately encapsidated into spherical particles of 20, 30 nm. The functions of CP thought to be important for the virus include: initiation of infection, stability of viral RNA, switching from minus to plus RNA, movement of the infectious material throughout the host, and encapsulation. The N-terminus of the AlMV CP specifically binds to the 3' noncoding region of all AlMV RNAs, requiring the AUGC repeats at the 3' end of viral RNAs and initiates the infection. The carboxyterminus of CP is required for the encapsidation of viral RNA. Earlier we have shown that AlMV CP carrying 37 amino acids at its N-terminus will preserve the biological activity and form the particles in vitro (Yusibov et al., J. Gen. Virol 77, 567 (1996)). Because of the ability of AlMV CP to form these particles in vitro and carry large peptides, the AlMV CP is used as an additional component to complement TMV expression system. In vitro transcripts of TMV carrying inserted sequences are used for the mechanical inoculation of tobacco plants. Within 10–14 days after inoculation, infected plant tissue can be used to determine the amount of protein in tissue, for purification of virus particles, and for the feeding experiments to test mucosal immunogenicity. For the latter, low alkaloid tobacco plants that can be fed to the animals are used to grow the recombinant viruses.

After infection with recombinant viral RNA coding for a fusion protein (AlMV capsid protein fused to an antigenic polypeptide), the infecting RNA is processed and the infection results in two types of viral particles:

1) recombinant TMV-recombinant viral RNA encapsidated with wild type TMV CP;

2) recombinant AlMV-non infectious AlMV particles consisting of subgenomic RNA coding for fusion protein (AlMV capsid protein fused to an antigenic polypeptide) and fusion protein.

The particles consisting of recombinant AlMV CP serve as antigen delivery and presentation systems. These particles have advantages over recombinant TMV particles that do not have AlMV or ilarvirus fusion capsid proteins. The use of AlMV or ilarvirus capsid protein allows the assembly of up to 100 amino acids presenting foreign antigenic or nonantigenic sequences into particles for effective antigen presentation. The TMV CP is capable presenting up to 25 amino acids. The larger peptides interferes with TMV assembly. Additionally, AlMV CP molecules each of which is fused to different antigenic polypeptides will assemble into multivalent particles carrying multiple antigens, which allows simultaneous immunization against multiple pathogens.

EXAMPLES

Example 1

Construction of Vectors and Method of Plant Transformation

Construction of Plasmids containing recombinant TMV carrying chimeric AlMV CP

Tobacco mosaic virus was used as a vector for the expression of chimeric genes. The plasmids B30Rz and AvB30Rz (Proc. Natl. Acad. Sci. U.S. 88, 7204 (1991)) containing the TMV genome and multiple cloning sites were a gift from Dr. William Dawson of Florida University. All fusion capsid proteins were made using AlMV CP where the first AUG codon (start codon for in vivo translation of AlMV CP) was exchanged for TCG to create an XhoI (CTCGAG) site for cloning and an RNA molecule defective in translation (an RNA molecule which does not have a continuous open reading frame that will support the synthesis of stable and detectable polypeptide in vivo or in vitro, pSPΔAUG, (Yusibov and Loesch-fries, Virology 208, 405 (1994)). For example, Peptides or proteins from human immunodeficiency virus (HIV) and from rabies virus were engineered as fusion with capsid protein of AlMV and cloned into B30Rz.

Construction of fusion protein consisting of full length AlMV CP and V3 loop of HIV-1MN strain A plasmid DNA containing sequences for HIV-1 envelope protein (env, 160) was used as a template for the polymerase chain reaction (PCR). (Such a plasmid can be made by cloning the cDNA of the HIV-1 MN strain containing gp120 sequences including the V3 loop by using PCR cloning into the PCRII vector (Invitrogen, Inc.) or other appropriate vector. The plasmid used here was supplied by David Weiner of U. Pennsylvania). PCR on the plasmid DNA containing sequences for HIV-1 envelope protein was performed using 5'-AGATCTCGAGATGAGTTCATCTGTAGAAATTAA-TTGTACA-3' as the first strand- and 5'-CGGCTCGAGCTACTAATGTTACAATG-3' as the second strand primers. The PCR products were digested by XhoI and ligated into pSPCPΔAUG linearized by XhoI. The ligation product, pSPCPMNV3, contained the DNA coding for the HIV V3 loop and full length AlMV CP. The translation initiation codon (AUG) was created upstream of the first codon (UGC, which codes for Cys) of the V3 loop so that the full length fusion protein will be read only from this codon. The clone also contained 5'- (37 nucleotides upstream of wild type AlMV CP translation start codon) and 3'- (192 nucleotides following AlMV CP stop codon containing AlMV origin of assembly) noncoding regions of AlMV CP. The segment of pSPCPMNV3 containing the DNA for HIV-1 V3 loop, the AlMV CP, and the 5'- and 3'-noncoding regions of AlMV CP, were excised by EcoRl and SmaI then ligated into B30Rz, that had been cleaved by XhoI, by blunt end ligation. The resulting plasmid was pBRzCPMNV3. This strategy (described for the cloning of V3 loop of HIV-1MN strain) was used to clone the V3 loop, vpr and vpu, of the HIV-1 NL 4.3 strain. The primers used in PCR reactions to obtain a specific sequences of these genes are listed in Table. 1. The PCR products were cloned into PSPΔAUG linearized by XhoI to fuse with AlMV CP and create chimeric protein. The resulting plasmids were named pSPCPNLV3, pSPCPNLVpr, and pSPCPNLVpu. The full length fusion protein carrying V3 loop, vpr, or vpu was introduced into B30Rz to generate plasmids, pBRzCPNLV3, pBRzCPNLVpr, and pBRzCPNLVpu. These plasmids contain full length TMV molecule and engineered fusion proteins subcloned under the subgenomic promoter of TMV CP.

TABLE 1

HIV-1 NL 4.3 V3 loop: 5' primer
AGA TCT CGA GAT GAG TTC ATC TGT AGA AAT TAA TTG TACA (SEQ ID NO:5)
HIV-1 NL 4.3 V3 loop: 3' primer
CGG CTC GAG CTA CTA ATG TTA CAA TG (SEQ ID NO:6)
HIV-1 NL 4.3 Vpr: 5' primer
GCA CTC GAG CAG ATG GAA CAA GCC CCA (SEQ ID NO:7)
HIV-1 NL 4.3 Vpr: 3' primer:
GCA CTC GAG GCG GAT CTA ATG GCT CCA TT (SEQ ID NO:8)
HIV-1 NL 4.3 Vpu: 5' primer
GCA CTC GAG GTG ATG CAA CCT ATA ATA GTA (SEQ ID NO:9)
HIV-1 NL 4.3 Vpu: 3' primer:
GCA CTC GAG GCC AGA TCA TCA ATA TCC CA (SEQ ID NO:10)
31DNV10C primers for rabies N protein (NV10c) and synthetic epitope (31D) presented as DNV10c:
31DNV10C: 5' primer
GCGCTCGAGATGTCCGCCGTCTACACCCGAATTATGATGAACGGAGGACG
ACTTAAGCGATACGAGGCAGCTGAAC (SEQ ID N0:11)
31DNV10C: 3' primer;
GCGCTCGAGTCGTCTGCTAGTGCCACGTCGGTAAGGGTAAGTTCAGCTGC
CTCGTATCGCTTAAGTCGTCC (SEQ ID NO:12)
31DG24 primers for linear epitope of rabies G protein (rg24) and synthetic peptide (31D) presented as DRG24:
31DG24: 5' primer
GCGCTCGAGATGTCCGCCGTCTACACCCGAATTATGATGAACGGAGGACG
ACTTAAGCGACCACCAGACCAGCTTG (SEQ ID NO:13)
31DG24: 3' primer;
GCGCTCGAGTCCTCTTCCACCACAAGGTGCTCATTTTCGTCGTGAAGGT
TCACAAGCTGGTCTGGTGGTCGCTTAAGTCGTCC (SEQ ID NO: 14)

Construction of fusion proteins consisting of full length AlMV CP and chimeric rabies epitopes: DNV10c and Drg24

DNV10c is a chimera of the linear epitope (NV10c) of rabies nucleocapsid protein and the synthetic peptide 31D. Drg24 is a chimera of the linear epitope (rg24) of rabies glycoprotein and the synthetic peptide 31D. NV10c and rg24 are the B cell determinants. Synthetic peptide 31D is the T cell determinant.

The linear epitopes of the N (NV10C) and G (g24) proteins of rabies virus were engineered as a chimeras with the synthetic peptide 31D and the chimeras fused with AlMV CP. Each chimera (DNV10c and Drg24) was synthesized by PCR using overlapping primers (Table 1) which serve as a template for each other. The primers are made in a way that the first strand and second strand primers has 18 homologous nucleotides that will anneal during PCR reaction. Thus each primer will serve as a template for other one and support the synthesis of new chain. The primers were created to synthesize known amino acid sequence. The PCR products resulting from these reactions were digested by XhoI and cloned into pSPCPΔAUG to fuse with AlMV.CP. The resulting plasmids were named as pSPCPDNV10c and pSPCPDrg24. The sequences for full length fusion capsid proteins and for 5'-3' noncoding regions were cut by EcoRI plus SmaI and cloned into B30Rz linearized by XhoI and subsequent blunt end ligation to create pBRzCPDNV10c, pBRzCPDrg24. All clones, described above (pSPCPMNV3, pSPCPNLV3, pSPCPNLVpr, pSPCPNLVpu, pSPCPDNV10c, and pSPCPDrg24), were subjected to in vitro translation and sequencing analysis before they were cloned into final vector (B30Rz).

Construction of chimeric ACP/TMV

Figure 1A:
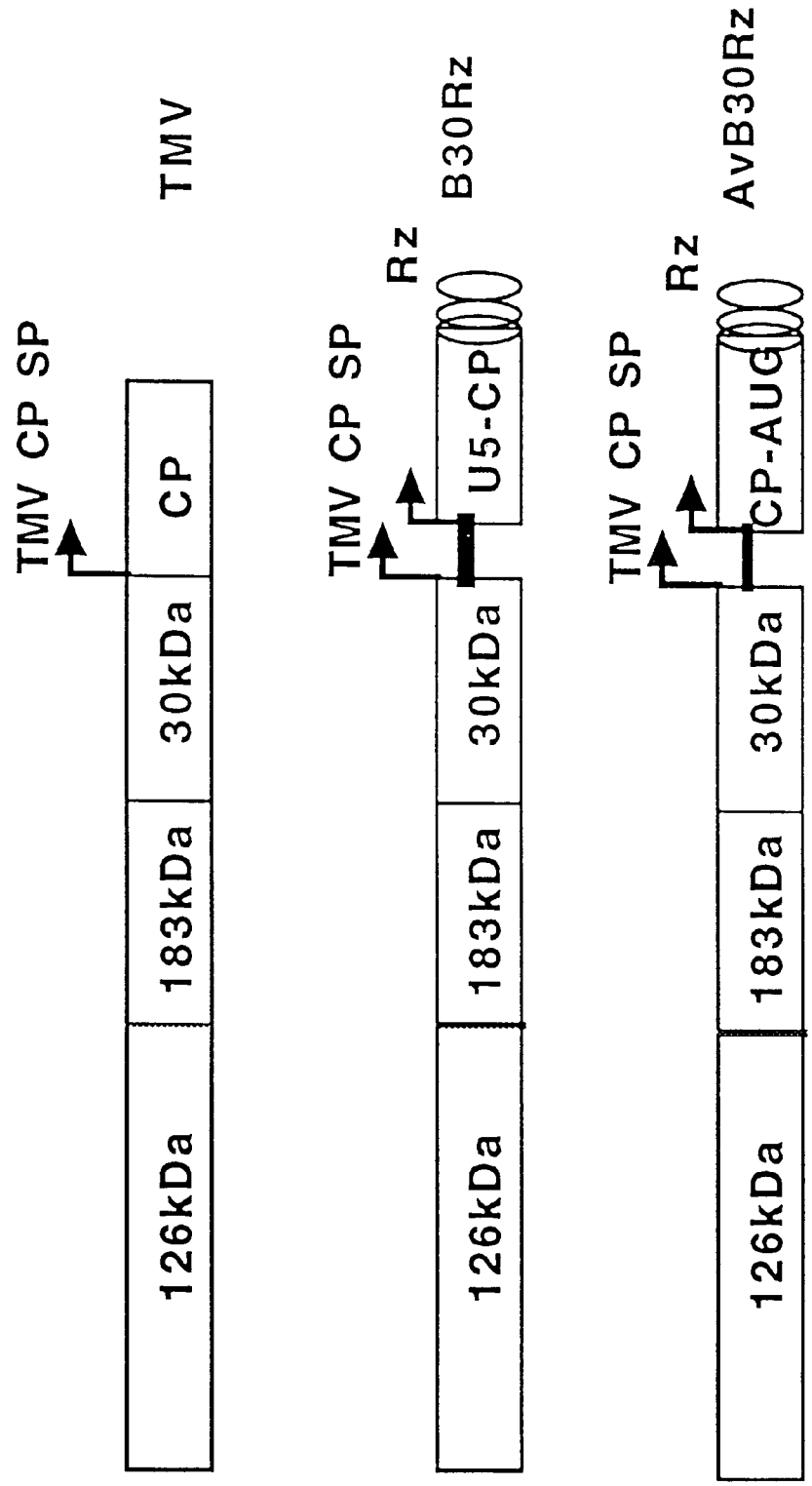
FIG. 1A. Schematic representation of the genome of TMV. The regions of the genome coding for the 126 kDa and 183 kDa proteins required for virus replication, the 30 kDa viral movement protein, and the CP (viral coat protein) are shown schematically. The arrow under "TMV CP SP" indicates the subgenomic promoter of TMV. The three connected ellipsoids under "pep" rerepresent the polypeptide fused to the AlMV CP. Rz- indicates ribozyme. B3O Rz- is a derivative of TMV. AvB30Rz- is a derivative of B3O Rz and is defective as to translation of coat protein.
Figure 1B:
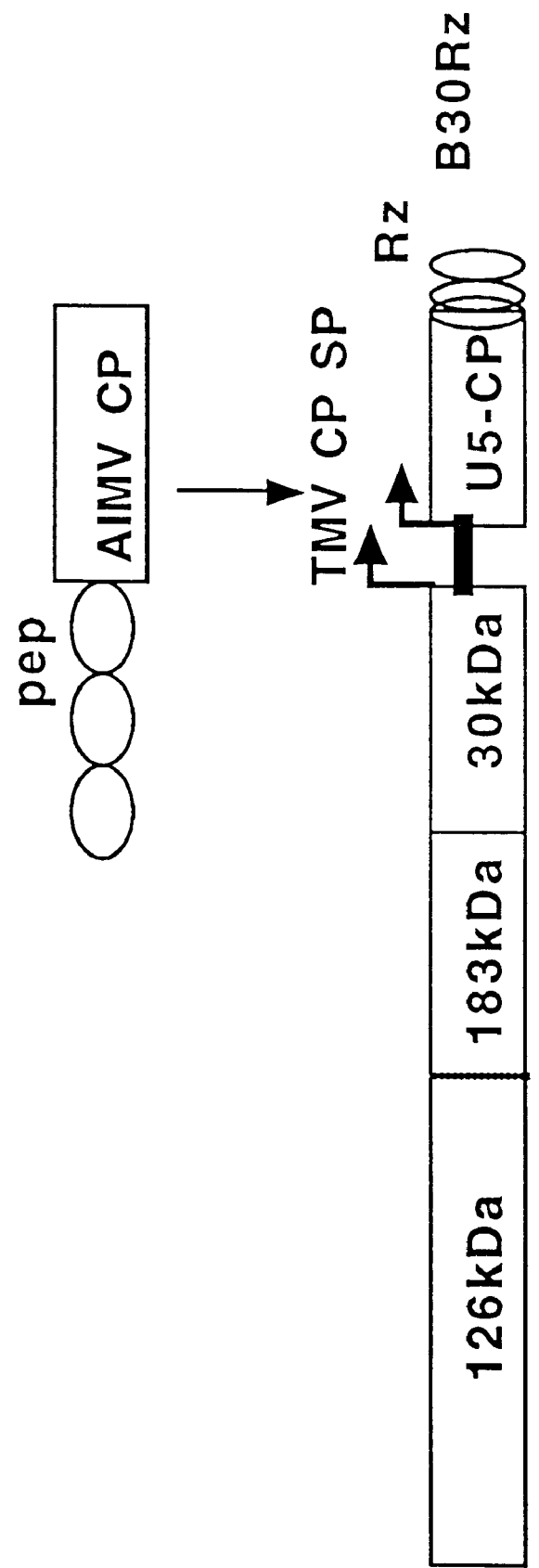
FIG. 1B. A schematic representation of cloning strategy: the cloning of chimeric AlMV CP into a TMV based vector. The sequences of polypeptides from HIV-1 and rabies virus are used as the "pep" to create recombinant viruses.

To engineer a chimeric TMV encapsidated with AlMV CP we used the TMV vector (Av/TMV) that had a nontranslatable coat protein. The Av/TMV was created in the laboratory of William Dawson of Florida University. The plasmid was derived from B30Rz used for the cloning described above. The schematic representation of the plasmid is given on FIG. 1A. To engineer the chimeric virus the wild type or recombinant AlMV CP (CP carrying Drg24) was cloned so as to be under the control of TMV CP subgenomic promoter. The AlMV CP was excised from pSP65A4 (Yusibov and Loesch-Fries, Proc. Natl. Acad. Sci. US 92, 8980 (1995)) by EcoRI plus SmaI and ligated into Av/TMV digested by XhoI by blunt ends to create the pAv/ACP. The pAv/ACPDrg24 was created identical to pBRzCPDrg24 using the primers described above and XhoI cloning site.

In vitro transcription and translation

In vitro transcripts of recombinant genes or recombinant TMV were synthesized using Promega T7 or SP6 RNA polymerase and CsCl purified plasmid DNA. The reaction was performed according to manufacturer guidelines. Transcripts were capped using RNA cap structure analog [m7G(5)ppp(5)G, Biolabs]. The transcripts were assayed by in vitro translation to determine the messenger activity of each RNA.

In vitro translation reactions were performed using a wheat germ cell-free translation system (Promega) and $^{35}$SMet (DuPont). The reactions were carried out as described by the manufacturer and the resulting products were separated by electrophoresis in a 13% SDS-polyacrylamide gel followed by autoradiography.

Preparation, inoculation and immunoassays of protoplasts

Protoplasts were isolated from axenic tobacco plants (*Nicotiana tabacum* var. *Xanthi-nc*) as described (Yusibov and Loesch-Fries, 1996) and inoculated with 3 μg of recombinant TMV transcripts per 1×10⁵ protoplasts using a polyethylene glycol procedure (Yusibov and Loesch-Fries, Proc. Natl. Acad. Sci. U.S. 1995). After inoculation the protoplasts were incubated on ice (15 minute) pelleted and washed twice with 10% mannitol. After final speen the protoplasts were resuspended in 1×AIOK medium (0.2 mM $KH_2PO_4$, 1 mM $KNO_3$, 1 mM $MgSO_4$, 1 μM KI, 0.1 μM $CuSO_4$, 10 mM $CaCl_2 \cdot 2H_2O$, pH 6.5) and incubated at low light conditions at 25–27° C. The protoplasts were collected 24 hr after inoculation and assayed by immunofluorescence using monoclonal antibodies to AlMV CP (Loesch-Fries & T. Hall, J. Gen. Virol., 47, 323 (1980)) to determine the accumulation of recombinant protein (immunofluorescent microscopy or Western analysis).

Immunoprecipitation of particles

The particles extracted from plant tissue which were coinfected with transcripts of recombinant virus were immunoprecipitated using monoclonal antibodies to the linear epitope of rabies G protein (rg24). Antibodies (Dietzschold et al., Virology 64, 3804 (1990)) were mixed with recombinant virus in a ratio 1:500 (w:w) and incubated at 4° C. with agitation for two hours. Within 2 hr the suspension of (50 μl) formalin-fixed staph A cells were add to the incubation mix and continued incubate at the same conditions for one more hour. After incubation was complete the cells were pelleted and washed three time with the original buffer in which the virus particles were stored (sodium phosphate buffer, pH 7.2). The final pellet was resuspended in a 50 μl of protein loading buffer and used for the Western analysis.

Western analysis

Protein preparations from virus infected tissue, purified virus samples or from immunoprecipitation were separated on SDS-PAGE electrophoresis and electroblotted on to nylon membrane using Towbins transfer buffer (0.025 M Tris, 0.192 M glycine, 20% methanol, pH 8.3) overnight at 33 mA. After blocking with milk (Kierkegarden) proteins were reacted with appropriate antibodies Westatin stain kit manufacturer (Sigma)).

Plant infection and virus isolation

Primary infection of tobacco leaves was initiated with in vitro transcription products of recombinant TMV strains, described above. Transcription products of recombinant virus were diluted 1:1 (final concentration: 15 mM) in 30 mM sodium phosphate pH 7.2 and applied to expending tobacco leaves (growing, 3–4 week old leaves). Inoculation was effected by gentle rubbing in the presence of carborundum (320 grit; Fisher, Pittsburgh, Pa.) to spread the inoculum and abrade the leaf surface. Inoculum was applied after the abrasive. Inoculated *N. bentamiana* plants were isolated in a greenhouse and maintained with normal watering and fertilization. To isolate the virus particles carrying recombinant protein from locally and systemically infected leaves of tobacco they were harvested 12 days post-inoculation. The leave tissue was frozen in liquid nitrogen and ground in prechilled mortar. Ground tissue was transferred into sterile tubes containing buffer (1 ml/1 g of tissue; 0.25 M sodium phosphate, pH 7.2) and resuspended by vortexing followed by centrifugation at 10,000 rpm for 15 minutes. All manipulations with samples were performed at 0 to 40° C. Upon centrifugation the supernatant was transferred into new tubes and virus particles were selectively precipitated in a buffer containing 4% polyethylene glycol (MW 15,000–20,000) and 50 mM NaCl for 2 hours. Polyethylene glycol is a component that precipitates virus particles. Then virus particles were pelleted at 10,000 rpm for 20 minutes. The pellet was resuspended in a 25 mM sodium phosphate buffer pH 7.2 and centrifuged once again under a similar conditions to separate possible plant debris and insoluble plant components. The supernatant (which contains virus) from this step was used for future experiments.

Example 2

Synthesis of Fusion Capsid Proteins

In vitro translation of fusion capsid proteins

Before cloning into the final vector (30BRZ) the recombinant genes were tested for the presence of a complete open reading frame of fusion capsid proteins by sequencing and/or by in vitro translation. Sequence analysis was performed using CsCl purified plasmid DNA containing original PCR fragments (pSPCPMNV3, pSPCPNLV3, pSPCPNLVpr, pSPCPNLVpu, pSPCPD10c, and pSPCPDrg24) and SP6 primer. CsCI purified recombinant plasmid (pSPCPMNV3, pSPCPNLV3, pSPCPNLVpr, pSPCPNLVpu, pSPCPD10c, and pSPCPDrg24). DNA containing engineered genes was digested by SmaI and used for the in vitro transcription. The capped transcripts of recombinant genes were synthesized using SP6 polymerase and translated in a wheat germ cell free translation system as described above. All tested transcripts had a messenger activity and directed the incorporation of $^{35}$SMet into polypeptides of expected size.

Translation of fusion capsid proteins in infected tobacco protoplasts

To assess the expression of fusion capsid proteins from TMV vector, the full length capped transcripts of recombinant virus were made and used for infection of tobacco protoplasts. 24 hr after inoculation with 3 µg of transcripts per $1 \times 10^5$, the protoplasts were collected and used for immunoassay and for the Western analysis. Immunofluorescent assay of fixed protoplasts where we used antibodies (Loesch-Fries and T. Hall, J. Gen. Virol., 47, 323 (1980) against AlMV CP for detection showed a significant amount of protein accumulation in an individual infected cell (Data not shown). To assess the size of expressed proteins and their reaction with specific antibodies the proteins were separated on SDS polyacrylamide gel, transferred to a nylon membrane, and reacted with the monoclonal antibodies to each peptide (results not shown) or to the AlMV CP (FIG. 2). All fusion capsid proteins migrated in a range of expected size (28–35 kDa) and reacted with monoclonal antibodies to the AlMV CP or to specific peptides. The difference in the size of fusion proteins is dictated by the difference in the size of each fused with AlMV CP peptide.

Expression of fusion capsid protein in infected plants

To assess the expression of recombinant protein in locally and systemically infected plant tissues the expending leaves of tobacco were inoculated with transcripts of recombinant TMV. Twelve days after inoculation, the virus was purified from locally and systemically infected leaves separately. In local infections, infection occurred in originally inoculated leaves. In systemic infection, the spread of virus was throughout the plant into new growing noninoculated leaves. Prior to purification 30–50 mg of infected tissue was used to determine if, together with TMV particles, the recombinant AlMV particles were assembled. The tissue was homogenized and the sap from it was applied on a carbon coated grid. The electron micrograph shows that spherical particles (presenting recombinant AlMV) were assembled upon infection with transcripts from all constructs (pBRzCPMNV3, pBRzCPNLV3, pBRzCPNLVpr, pBRzCPNLVpu, pBRzCPDNV10c, and pBRzCPDrg24). FIG. 3 presents the results of negative staining of particles (wild type B30Rz and recombinant BRzCPDrg24) using 2% urea acetate.

Western blot analysis of purified virus samples demonstrated the presence of fusion capsid proteins in samples from both locally and systemically infected leaves (FIG. 4). This indicated that the recombinant virus was viable and it retained the fusion capsid protein during systemic movement through the plant.

Infection of tobacco plants with pAv/ACP and pAv/ACPDrg24

The in vitro transcripts of pAv/ACP or pAv/ACPDrg24 were used for inoculation of tobacco plants. Within eight days the tissue samples were collected to assess the systemic spread of virus in noninoculated leaves. Western analysis (data not shown) detected the wt (ACP) or recombinant (ACPDrg24) protein in a systemic noninoculated leaves of tobacco indicating that AlMV CP supported the systemic spread of CP defective TMV. The plants inoculated with transcripts of the vector itself (pAv/TMV) did not show any systemic symptoms on tobacco plants even 20 days after inoculation.

Assembly of recombinant AlMV particles presenting epitopes from different pathogens Samples of infected leaf tissues from pBRzCPMNV3, pBRzCPNLV3, pBRzCPDNV10c, and pBRzCPDrg24-infected plants were taken, combined and used for the infection of tobacco plants. The virus particles were purified 12 days after inoculation and assessed for co-assembly of recombinant AlMV CPs from different constructs. The virus particles were immunoprecipitated using monoclonal antibodies to the linear epitope of rabies G protein (rg24) and formalin fixed Staph A cells. Immunoprecipitation products were separated by SDS polyacrylamide gel electrophoresis (above) and used for the Western blot analysis. The separated proteins were reacted to the monoclonal antibodies for the AlMV CP, antibodies against the linear epitopes of rabies N and G proteins, and antibodies against V3 loop of HIV1 MN strain (National Institute of Allergy and Infectious Diseases AIDS Research and Reference Reagent Program. #1728 Antibody to HIV-1 V3). All antibodies reacted with the immunoprecipitation product after gel separation (FIG. 5) indicating that upon co-infection AlMV CP molecules will assemble into multivalent particles presenting antigenic epitopes from different pathogens. The larger molecular weight bands seen in FIG. 5 represent protein dimers similar to those of control virus (AlMV CP).

Example 3

Immunization of Mice with AlMV/TMV Construct Expressing the Drg24 Peptide Epitope of Rabies Glycoprotein Eight-week old female Swiss-Webster, outbred mice were immunized with 10 µg per dose of recombinant TMV virus engineered to express the rg24 epitope of rabies glycoprotein (Drg24-A/TMV). Three immunizations of 0.1 ml were administered intra-peritoneally at intervals of 2 weeks each with and without complete Freund's adjuvant (CFA) at a 1:1, vol:vol ratio. An equal quantity of a mixture of wild type AlMV plus TMV was used with and without CFA as controls. Ten-to-fourteen days after each immunization, serum samples were obtained from individual mice and rabies virus-specific antibody titers assessed. Antigen-specific antibody analysis of serum was performed using a solid phase enzyme-linked immunoabsorbant assay (ELISA). ELISA plates (Nunc Polysorp, Denmark) were coated with 100 µl per well of inactivated ERA-strain rabies virus (5 µg/ml in Phosphate-buffered saline) overnight at room temperature (RT; about 25° C.). Coated plates were washed 3× with PBS-Tween (0.05%) and then blocked with 5% dried milk in PBS at RT for at least 1 hour. A series of dilutions of sera were added to the plates (30 μl/well) for 2 to 4 hours at RT. The plates were then washed 3× with PBS-Tween and peroxidase-conjugated secondary antibodies (goat anti-mouse IgG, either whole molecule or gamma chain specific) were added (100 μl per well) at a final dilution of 1:2000 in PBS, for 1 hour at RT. Plates were then washed 5× with PBS-Tween and TMB substrate added (100 μl/well) in phosphate-citrate buffer containing urea, for 30 min at RT in the dark. The reaction was stopped with 2M $H_2SO_4$ (50 μl per well) and the color change resulting from bound specific antibody measured at 450 nM in an ELISA plate-reader (Bio-Tek, Winooski Vt.). The results, expressed in O.D. units, are shown (FIG. 6A). Eighty percent of mice immunized with particles carrying Drg24 had rabies-specific antibodies (FIG. 7). Specific neutralization of rabies virus was assessed using a modified rapid fluorescent focus forming assay (FIG. 6B). Serum was inactivated by treatment for 30 minutes at 56° C. and diluted in MEM medium supplemented with 10% fetal bovine serum (FBS) to a starting dilution of 1/5. The 1/5 serum dilution was further diluted serially 1/2 (1 volume plus 1 volume diluent) in 96 well plates (Nunc) such that each well contained 50 μl of the titrated serum. Thirty μl of a preparation of rabies CVS-11 virus was added to each well. The rabies virus solution was prepared such that 30 μl diluted with 50 μl of medium and 30 μl of BHK indicator cells ($1.5 \times 10^6$/ml) contained sufficient virus to cause infection of 80 to 90% of the cells in monolayer cultures after 20 hours. The 96-well plates containing the serum dilutions and rabies virus were incubated for 1 hour at 37° C. prior to being carefully mixed with 30 μl of BHK indicator cells ($1.5 \times 106$/ml). Ten μl of each of these mixtures was transferred to the wells of Terasaki plates (Nunc). The Terasaki plates were incubated for 20 hours at 37° C. in a humidified atmosphere of 95% air and 5% $CO_2$. The plates were then washed 3× with PBS and the cells fixed by the addition of ice-cold acetone (90%) for 20 minutes. The plates were then air dried and 5 μl of a 1/40 dilution of fluorescein-conjugated rabies virus-specific antibody (Centocor) added to each well for 40 min. at 37° C. The plates were then washed 3× with water and the percentage of infected BHK cells evaluated using a fluorescent microscope (Leitz). FIG. 6B shows the presence of neutralizing antibodies in sera.

Example 4

AlMV Constructs Not Involving TMV Nucleic Acid

AlMV constructs free of TMV RNA analogous to those described above are constructed in a matter analogous to the TMV recombinant constructs. AlMV nucleic acid is substituted for the TMV RNA. The structure of the AlMV genome is published and the required functions coded for by the AlMV genome have been mapped. (Bol et al., Virology 46, 73 (1971); Bol etal., Virology 58, 101 (1974)).

What is claimed is:

1. A process of administering a polypeptide to an animal, the process comprising the steps of:

(1) infecting a plant cell with recombinant plant virus nucleic acid that will be processed in a plant cell to produce a fusion capsid protein, said fusion capsid protein comprising a plant virus capsid protein and the polypeptide, such that the polypeptide is fused to the amino terminus of said plant virus capsid protein, wherein said polypeptide is not a plant virus capsid protein, said plant virus capsid protein being an alfalfa mosaic virus (AlMV) capsid protein or ilarvirus capsid protein, wherein said recombinant plant virus nucleic acid comprises an AlMV or ilarvirus nucleic acid vector and further comprises nucleic acid coding for the polypeptide such that the polypeptide will be fused to the amino-terminus of the AlMV capsid protein or ilarvirus capsid protein, said infecting resulting in an infected cell;

(2) cultivating the infected cell under conditions where said infected cell makes the fusion capsid protein, and (3) administering the fusion capsid protein to an animal, thereby inducing the production of antibodies against at least the polypeptide in said animal.

2. The process of claim 1 wherein step (2) takes place in a plant and in step (3) the fusion capsid protein is administered as part of a plant or plant material to an animal.

3. The process of claim 1 wherein in step (3) the fusion capsid protein is extracted in purified form from a plant and administered as a protein substantially free of other compounds of the plant.

4. The process of claim 1 wherein the polypeptide is a rhabdovirus polypeptide.

5. The process of claim 1 wherein the polypeptide is a human immunodeficiency virus polypeptide.

6. The process of claim 1 wherein the animal is a mammal.

7. The process of claim 1, the process comprising the steps of:

(1) infecting a plant cell with a plurality of recombinant plant virus nucleic acids of claim 1 that will be processed in a plant cell to produce a plurality of fusion capsid proteins, each comprising a different polypeptide that is not a plant virus capsid protein, and each further comprising an AlMV capsid protein or ilarvirus capsid protein, thereby resulting in an infected cell;

(2) cultivating the infected cell under conditions where said infected cell makes said plurality of fusion capsid proteins; and (3) administering said plurality of fusion capsid proteins to an animal, thereby inducing the production of antibodies against the different polypeptides in said animal.

8. A process for producing a polypeptide, the process comprising the steps of:

(1) infecting a plant cell with recombinant plant virus nucleic acid that will be processed by a plant cell to produce a fusion capsid protein, said fusion capsid protein comprising a plant virus capsid protein and the polypeptide such that the polypeptide is fused to the amino terminus of said plant virus capsid protein, said plant virus capsid protein being an AlMV or ilarvirus capsid protein, said polypeptide not being a plant virus capsid protein, said infection resulting in an infected cell;

(2) cultivating the infected cell under conditions where said infected cell makes the fusion capsid protein.

9. The process of claim 1 wherein the polypeptide is 26 to 100 amino acids in length.

10. The process of claim 1 wherein, in step (1) two or more different fusion capsid proteins are produced each with a polypeptide of different amino acid sequence, wherein in step (2) said fusion capsid proteins are produced, and wherein in step (3) said fusion proteins are administered.

11. The process of claim 1 wherein in step (2) the capsid protein fused to the polypeptide is assembled into a particle.

12. The process of claim 1 wherein the virus capsid protein is an AlMV capsid protein.

* * * * *